(12) United States Patent
Schultz

(10) Patent No.: US 10,426,873 B2
(45) Date of Patent: Oct. 1, 2019

(54) EVACUATION SYSTEM

(71) Applicant: Nascent Surgical, LLC, Eden Prairie, MN (US)

(72) Inventor: Leonard S. Schultz, Bloomington, MN (US)

(73) Assignee: Nascent Surgical, LLC, Eden Prairie, MN (US)

( * ) Notice: Subject to any disclaimer, the term of this patent is extended or adjusted under 35 U.S.C. 154(b) by 1152 days.

(21) Appl. No.: 14/245,259

(22) Filed: Apr. 4, 2014

(65) Prior Publication Data

US 2014/0303576 A1    Oct. 9, 2014

Related U.S. Application Data

(60) Provisional application No. 61/808,877, filed on Apr. 5, 2013, provisional application No. 61/887,026, filed on Oct. 4, 2013.

(51) Int. Cl.
| | |
|---|---|
| *A61M 1/00* | (2006.01) |
| *A61B 18/04* | (2006.01) |
| *A61M 31/00* | (2006.01) |
| *A61M 37/00* | (2006.01) |
| *B65B 1/04* | (2006.01) |

(Continued)

(52) U.S. Cl.
CPC ........... *A61M 1/0035* (2014.02); *A61B 18/04* (2013.01); *A61M 1/0031* (2013.01); *A61M 1/0094* (2014.02); *A61B 2018/00595* (2013.01); *A61B 2018/00601* (2013.01); *A61B 2018/00982* (2013.01); *A61B 2217/005* (2013.01); *A61B 2218/006* (2013.01); *A61B 2218/008* (2013.01)

(58) Field of Classification Search
CPC ........ A61M 1/00; A61M 31/00; A61M 37/00; B67C 3/16; B65B 1/04; B65B 31/04
See application file for complete search history.

(56) References Cited

U.S. PATENT DOCUMENTS

| | | |
|---|---|---|
| 4,921,492 A | 5/1990 | Schultz et al. |
| 5,015,243 A | 5/1991 | Schifano |

(Continued)

FOREIGN PATENT DOCUMENTS

| | | |
|---|---|---|
| WO | WO 99/29250 | * 12/1977 |
| WO | WO 99/29250 A1 | * 12/1977 |

OTHER PUBLICATIONS

International Search Report and Written Opinion for PCT Application No. PCT/US2014/032953 dated Aug. 25, 2014. (12 pages).

*Primary Examiner* — Tatyana Zalukaeva
*Assistant Examiner* — Ilya Y Treyger
(74) *Attorney, Agent, or Firm* — Dorsey & Whitney LLP

(57) ABSTRACT

An evacuation system and method for removing and/or treating gaseous and/or particulate byproducts of surgical procedures includes an end effector such as a side vent trocar, an operating room tower or the equivalent, a disposal vessel, a vacuum source and optionally a filter. The end effector may be coupled to the tower by a conduit, the tower may be coupled to the collection tank by a conduit, and the collection tank may be coupled to the vacuum source. Gaseous and/or particulate byproducts may flow from the surgical site through the trocar, conduits, tower tank and filter, and the flow may be regulated at least in part by the components of the system.

20 Claims, 3 Drawing Sheets

(51) Int. Cl.
  *B67C 3/16*    (2006.01)
  *A61B 18/00*   (2006.01)

(56) References Cited

U.S. PATENT DOCUMENTS

| | | | |
|---|---|---|---|
| 5,458,138 A * | 10/1995 | Gajo | A61M 1/0001 |
| | | | 128/205.12 |
| 5,688,256 A | 11/1997 | Surratt et al. | |
| 5,968,032 A | 10/1999 | Sleister | |
| 6,524,307 B1 | 2/2003 | Palmerton et al. | |
| 6,592,543 B1 | 7/2003 | Wortrich et al. | |
| 7,207,977 B2 | 4/2007 | Thompson et al. | |
| 7,612,492 B2 * | 11/2009 | Lestician | A23L 3/26 |
| | | | 313/483 |
| 7,717,890 B2 | 5/2010 | Drogue et al. | |
| 9,615,852 B2 * | 4/2017 | Farin | A61B 17/3421 |
| 2007/0135779 A1 * | 6/2007 | Lalomia | A61M 1/0005 |
| | | | 604/319 |
| 2007/0249990 A1 | 10/2007 | Cosmescu | |

* cited by examiner

EVACUATION SYSTEM

CROSS-REFERENCE TO RELATED APPLICATIONS

This application is a non-provisional application of U.S. Provisional Application Ser. Nos. 61/808,877, filed on Apr. 5, 2013, entitled "Smoke Evacuation System;" and 61/887,026, filed on Oct. 4, 2013, entitled "Smoke Evacuation System," the contents of each of which are incorporated by reference in their entirety.

TECHNICAL FIELD

The present disclosure relates to smoke evacuation systems, and more particularly to evacuation systems operable to control suction levels for use in removing surgical byproducts such as smoke and body fluids in laparoscopic settings while employing vacuum devices adapted for open surgery.

BACKGROUND

This invention relates to equipment, systems and methods for the removal and/or treatment of gaseous and/or substantially gaseous material. Such material includes, but is not limited to aerosol and particle byproducts of surgical procedures and any procedures involving cutting, heating or burning, and may include, for example, chemicals, ultrasonic vapors, particles, and ion dust particles. More particularly, the present invention relates to an evacuation system that efficiently removes smoke, odor, vapor, particles or plumes released by chemicals or produced by the use of lasers, sonic cutting and/or cautery or other surgical techniques or instruments at a surgical site.

Heating and/or burning of tissue during surgical procedures has become commonplace. An unwanted byproduct of such heating and/or burning, however, is the smoke and/or aerosol generated thereby. Smoke plumes can obscure the surgeon's field of vision and the odor generated is unpleasant and distracting to the entire surgical team and to the patient, if awake. Moreover, the smoke plume may contain infectious agents that present a danger to persons in the operating room, and which can leave a lingering contamination within the operating area. Chemical vapor may be irritating to the respiratory tract of those who inhale it and may be carcinogenic.

Smoke evacuation and filtering systems have been developed to remove smoke plumes from surgical sites and/or chemical vapors from a work environment. Such systems typically include a vacuum source or generator, a conduit connected to the vacuum source and a suction wand or end effector connected to the conduit for being placed at or near the site at which the plumes or vapors are generated. Various filtration systems have been used in conjunction with such systems to remove odor and infectious agents. Known evacuation systems are disclosed in U.S. Pat. No. 4,921,492 (Schultz) and U.S. Pat. No. 7,207,977 (Thompson), the disclosures of which patents are incorporated herein by reference. U.S. Pat. No. 5,015,243 (Schifano) discloses another smoke evacuator for drawing smoke and air from around a surgical site as smoke is produced.

In some embodiments, current state of the art devices for removal of smoke and/or other byproducts generated during laparoscopy are devices for passive evacuation and filtration wherein an ULPA-activated charcoal filter is attached to the side vent of a trocar. Flow and filtration rely at least in part on the pressure difference between the interior of the abdomen and outside of the body to generate a flow to remove and filter the smoke. In some embodiments, depending upon the system and/or the method of flow restriction and/or regulation, flow rates of smoke-laden carbon dioxide gas is 6-10 liters per min. from the abdomen, through the filter and into ambient air.

Today's relentless reduction in reimbursement by insurance agencies for hospital invoices make cost-effective methods for surgical procedures imperative. For example, a $25/filter used in one and a half to two million cases/year creates a healthcare expense of $37.5-50M/year.

While known smoke evacuation systems and end effectors, e.g., those of the Schultz, Thompson and Schifano type, are well-suited for their intended purposes, there is room for improvement.

SUMMARY

The present invention provides a system for actively removing or evacuating smoke, chemical vapors, aerosols, particles, gaseous or generally gaseous material, liquids and/or fluids, including fluids with entrained particles or other material. The system may be used and/or adapted for removing such substances from surgical sites, workstations and manufacturing assemblies or processing sites.

Embodiments of a smoke evacuation system and method, including an evacuator, in accordance with the present invention are designed to efficiently and quietly remove and/or treat smoke or other aerosols, including smoke or bioaerosols (e.g. a mixture of body fluids, irrigant and gas) generated during surgical procedures, and in some embodiments can be used at a surgical site without constant attention or manipulation by the surgeon or an attendant.

In some embodiments, the present invention comprises a vacuum smoke evacuator for coupling to a vacuum source for withdrawing generally gaseous byproducts, including smoke, fine particulate matter, air and the like, from a surgical or commercial site.

In some embodiments, a system and method in accordance with the present invention would save money over current systems, potentially saving, based on anticipated increases to 4 million cases/year, $80M/year, e.g. by not needing to continually and/or as frequently replace expensive HEPA or ULPA filters. In addition, the system of the present invention would allow substantially complete removal of smoke and/or particles from the operating room including what remains after ULPA filtration, namely, nanoparticles or ultrafine particles of less than 100 nanometers in diameter. These are the particles responsible for causing systemic diseases as a result of chronic exposure in operating rooms where health care personnel, e.g. nurses, technicians, anesthetists and physicians, surgical assistants, careers may span 20-30 years of exposure.

In some embodiments, an evacuation system in accordance with the present invention includes suitable conduits, flow regulators, restrictors and/or valves, end effectors or nozzles and/or connection features, e.g., to allow for suitable flow through the system and for coupling the system to a source of low pressure or vacuum.

According to one implementation, an evacuation system for surgical settings includes a vacuum source configured to generate a negative pressure for delivering a level of suction for removing smoke during open surgery. A flow regulator device fluidly couples to the vacuum source and includes a vacuum port, an inlet port, and a flow rate adjuster. The vacuum port is adapted to fluidly couple to the vacuum source, the inlet port is adapted to fluidly couple to an end effector, the vacuum port and the inlet port are fluidly coupled, and the flow rate adjuster is operable to adjust a level negative pressure delivered by the vacuum source to the inlet port to a reduced suction level. Consequently, the end effector receives a level of active suction for removing smoke from a body cavity during laparoscopic surgery. Particularly, the maximum level of suction allowed for laparoscopic surgical settings is less than the level of suction typically provided in open surgical settings. More specifically, and according to another implementation, the vacuum source may be configured to generate a negative pressure for delivering a level of suction of at least 25 cubic feet per minute ($ft^3$/min), whereas the end effector, by virtue of its connection to the flow regulator device, receives a level of suction for removing smoke from a body cavity of up to 0.35 $ft^3$/min (i.e., up to 10 liters per minute), which is nearly two orders of magnitude less than the level of suction delivered by the vacuum source.

According to yet another implementation, the evacuation system for surgical settings may include the aforementioned vacuum source and flow regulator device, as well as a disposal vessel configured to hold fluid byproducts from surgery; a decontamination area configured to decontaminate gaseous byproducts from surgery; an end effector configured for insertion into a body and for removing smoke from a body cavity during laparoscopic surgery; and a fluid pathway fluidly coupling the vacuum source, the disposal vessel, the decontamination area, the flow regulator device and the end effector. In this implementation, the vacuum port of the flow regulator couples to the vacuum source, the inlet port is adapted to fluidly couple to the end effector, the vacuum port and the inlet port are fluidly coupled, and the flow rate adjuster is operable to adjust a level negative pressure delivered by the vacuum source to the inlet port to a reduced suction level such that the end effector receives a level of active suction for removing smoke from a body cavity during laparoscopic surgery.

It should be appreciated that features of any of the embodiments of the present invention may be selectively combined to adapt the system for a variety of situations and surgical procedures.

Other features and advantages of the smoke evacuation system and method of the present invention will become more fully apparent and understood with reference to the following description and accompanying drawing and claims.

DETAILED DESCRIPTION

Figure 1A:
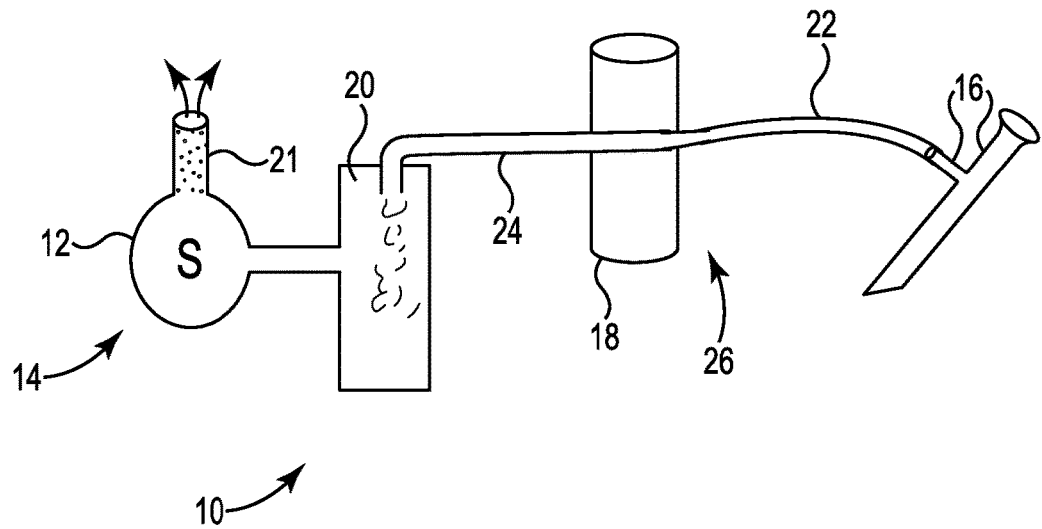
FIG. 1A illustrates an embodiment of a smoke evacuation system according to implementations of the present disclosure.
Figure 1B:
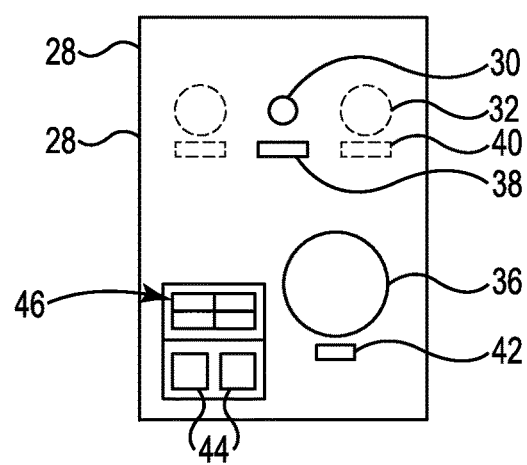
FIG. 1B illustrates a portion of the smoke evacuation system according to the implementation of FIG. 1A.

Overview: The accompanying drawings and this description depict and describe embodiments of the evacuation systems and methods of the present invention. Any reference to "the invention" herein shall not be construed as a generalization, limitation or characterization of any subject matter disclosed herein and shall not be considered to be an element or limitation of any appended claim except if and/or where explicitly recited or stated. As used herein, the term surgical site is intended to encompass places where an incision or puncture is to be made in the skin or where other surgical operations or procedures are performed or to be performed. With regard to fastening, mounting, attaching or connecting the components of the present invention to form the system, unless specifically described otherwise, such are intended to encompass conventional fasteners such as machine screws, nut and bolt connectors, machine threaded connectors, snap rings, hose clamps such as screw clamps and the like, rivets, nuts and bolts, toggles, pins and the like. Components may also be connected by adhesives, glues, heat sealing, snap fitting, welding, ultrasonic welding, and friction fitting or deformation, if appropriate. Unless specifically otherwise disclosed or taught, materials for making components of the present invention may be selected from appropriate materials such as metal, metallic alloys, natural and manmade fibers, vinyls, plastics and the like, and appropriate manufacturing or production methods including casting, extruding, molding and machining may be used.

Any references to front and back, right and left, top and bottom and upper and lower are intended for convenience of description, not to limit the present invention or its components to any one positional or spatial orientation.

Surgical sites are generally of two types: open surgical or laparoscopic. During open surgeries, smoke and vapors are produced as a result of burning or lasering of tissue. Consequently, suction devices are used proximate the surgical opening, and are typically hand-held suction devices, such as wands. During laparoscopic surgeries, smoke and vapors again are produced and become trapped within the surgical site and require removal to provide visibility to the surgical site. Thus, active suction is commonly used to evacuate the smoke and vapors from a body cavity while the laparoscopic surgery takes place.

Hand-held suction devices and laparoscopic suction devices have differing suction requirements. Particularly, hand-held devices used during open surgeries require a higher suction rate compared to suction rates allowed in laparoscopic surgery. For instance, vacuum sources for open surgeries may deliver negative pressures that generate a suction rate of at least 25 $ft^3$/min; and in contrast, vacuum sources for laparoscopic surgeries typically deliver negative pressures that result in a suction rate of about 0.35 $ft^3$/min (i.e., about 10 liters per minute). If a higher suction rate were used during laparoscopic surgery the patient would be at risk of having intact body tissue such as bowels suctioned, which can damage or destroy the intact tissue. Consequently, in prior approaches, dedicated conduits were used to connect to each of the hand-held suction devices and the laparoscopic devices, and each were joined to separate types of vacuum sources. For instance, devices used in open surgery were joined to a vacuum source having a relatively higher suction level, while devices used in laparoscopic surgeries were joined to a vacuum source having a relatively lower suction level. However, according to implementations of the present disclosure, a flow regulator device may couple a laparoscopic suction device to a single vacuum source adapted to deliver a higher suction level, while the flow regulator regulates the suction level to a lower suction level to enable a vacuum source to be used in laparoscopic surgical settings that otherwise would generate a suction level at the end effector that is unsafe for use in such settings. According to further implementations, the flow regulator device may additionally couple to hand-held suction devices for use with the same vacuum source and may be used in open surgical settings.

Accordingly, the vacuum sources applicable to the present disclosure may be almost any vacuum source adapted for use during open surgeries for delivering high suction rates. For instance, the vacuum source may be a self-contained vacuum unit commonly found in operating rooms such as LEVs (local exhaust ventilators) as made by Buffalo Filter, Conmed, Covidien, or may by a vacuum connection that is arranged through tubing to a site remote from the operating room.

Detailed Description of the Figures:

Referring to FIG. 1A, an embodiment of an evacuation system 10 is depicted in accordance with implementations of the present invention. The evacuation system 10 is generally found within an operating room or other area where surgeries are conducted and are used to evacuate byproducts of surgery such as smoke and fluids containing potentially harmful particulates, and both laparoscopic and open surgeries may be conducted using the evacuation system 10.

The evacuation system 10 includes a suitable vacuum source 12, e.g. a vacuum port. It further includes a filtration assembly 14; an end effector 16 such as a side vent trocar; a tower connector device 18 and/or the substantial equivalent, e.g., used to centralize and/or organize electrical connections and/or displays, tubes, outlets, etc. in an operating room; a disposal vessel 20 such as a decontamination area or a collection tank; and a filter 21. The end effector 16 is coupled to the tower connector device 18 by a conduit 22, the tower connector device 18 is coupled to the disposal vessel 20 by a conduit 24, and the disposal vessel 20 is coupled to the vacuum source 12. According to certain implementations, a flow regulator device 26, restrictor, valve or other suitable flow affecting arrangement, e.g., a suitably dimensioned connector, between the conduit 22 and tower connector device 18, is associated with the tower connector device 18 and is used to regulate negative pressure and therefore suction delivered to an end effector 16 from the vacuum source 12. In some implementations, the flow regulator device 26 may be associated with the end effector 16 or interposed between the tower connector device 18 and the trocar 16. In further implementations, the flow regulator device may be associated with the vacuum source 12, or interposed between the vacuum source 12 and the end effector 16, and the tower connector device 18 may or may not be present in such an evacuation system. Accordingly, the evacuation system 10 may include the devices depicted in FIG. 1A, or some of the devices may be removed or may be substituted without departing from the present disclosure.

The vacuum source 12 generates a negative pressure for delivering a level of airflow or suction at a rate adapted for open surgery, such as at a rate of at least 25 ft$^3$/min. As described, the vacuum source 12 is one that is generally used in open surgical settings where the level of suction required to remove smoke and fluids from the operating room is high, and in some implementations, may deliver a rate of suction of up to 60 ft$^3$/min. In some cases, the vacuum source 12 of the present disclosure may differ from in-wall suction units that operate with a suction rate of about 5-7 ft$^3$/min.

The filtration assembly 14 may be of the type commonly used in surgical settings and may be a stand-alone unit or may be integrally formed with or form a component of the vacuum source 12 or another component of the evacuation system 10. The filtration assembly 14 may include an ultra-low penetration air ("ULPA") filter, a high-efficiency particulate absorption ("HEPA") filter, a baffle, or other device used in decontamination processes and/or in removing particulates from fluid and/or air. The filtration assembly 14 may fluidly couple to the vacuum source 12, and during operation of the vacuum source 12, the negative pressure generated may cause the gaseous and/or particulate byproducts to flow to the filtration assembly 14, where the byproducts may be trapped while allowing filtered gasses and/or fluids to pass through the filtration assembly. The filtration assembly may thus ensure that potentially harmful vapors and particulates are separated from gasses and/or liquids that lead to the vacuum source. In some implementations, the filtration unit 14 may be disposable, e.g., a single-use arrangement, or may be reusable and replaceable.

The end effector 16 used in connection with the evacuation system 10 may be configured for use in laparoscopic settings and thus may be insertable through skin and into a body cavity of the patient where smoke plumes or vapors are generated. In some implementations, the end effector 16 may be a side vent trocar or suction-irrigation tube with one or more trumpet valves. End effectors may be extruded from a single piece of material, e.g., a unitary piece of synthetic resin or similar extrudable material, and may be advantageously and hygienically disposed of after a single use, without the necessity of handling contaminated material. The end effector 16 may be used in combination with an insufflator, which is generally used within the body cavity to inflate the cavity with carbon dioxide gas and provide positive pressure to maintain the body cavity in an inflated space during the laparoscopic procedure.

In addition to the end effectors used in laparoscopic settings, end effectors commonly used in open surgical settings may be provided according to certain implementations, for instance where the flow regulator device 26 includes inlet ports for receiving end effectors used in open surgery. Such end effectors may include wands, electrosurgical 'pencils' or 'pens' as well as the miniSquair® by Nascent Surgical.

The tower connector device 18 may generally be a device commonly found in operating rooms and may be used to centralize and/or organize electrical connections and/or displays, tubes, and ports (e.g., outlets and inlets) in an operating room. The tower connector device may include ports (inlets and outlets) adapted to be coupled to the vacuum source 12 and one or more end effectors, such as end effector 16, or conduit structures leading to the end effectors. Any suitable coupling or connection methods may be used in joining the ports to other devices including "quick-release"-type connectors, Leur-type, detent-type connectors, screw-type connectors or bayonet-type connective structures, and friction fitting. The coupling connections may include or may integrally form sealing components for facilitating the formation of a seal between the tower connector device 18 and the vacuum source 12 or another device associated therewith, e.g., the end effector 16. Sealing components may include but are not limited to O-rings and v-rings. The ports or other fluid connections coupled to the vacuum source 12 and other devices associated with the vacuum source 12 may be male or female connections defined by rigid or semi-rigid materials such as plastic, metal or glass that are capable of withstanding negative pressure and airflow without collapsing or substantially deforming. Additional components of the tower connector device 18 may be associated with a faceplate 28 and are described below.

The disposal vessel 20 may be used to hold and/or decontaminate fluid or particulate byproducts from surgery.

The disposal vessel 20 is generally arranged between the vacuum source 12 and the end effector 16 and traps fluids and particulates received from the end effector 16 prior to reaching the vacuum source 12, or the filtration assembly 14 when present. For instance, the disposal vessel may be configured as a decontamination area used to decontaminate gaseous byproducts, fluid byproducts or both through ultraviolet treatment. In some implementations, the disposal vessel 20 may additionally function as the filtration assembly 14. In addition, the disposal vessel 20 may be disposable, e.g., a single-use arrangement, or may be reusable and replaceable. In some implementations, the disposal vessel 20 may be used in combination with the system or components thereof described in U.S. Pat. No. 7,717,890, entitled "Fluid and Bioaerosol Management Vacuum Connector and System," and issued on May 18, 2010, the entire contents of which is incorporated by reference herein in its entirety.

The conduits 22 and 24 may be configured for coupling the various devices of the evacuation system of the present disclosure. With reference to FIG. 1A, the conduit 22 may be adapted for coupling the end effector 16 to an inlet port of the tower connector device 18 and may be sized and shaped for laparoscopic use. For instance, the conduit 22 may be tubing with a ⅜ inch diameter that couples to a laparoscopic inlet port of the tower connector device 18 and to a side vent portion of a trocar or other end effector used in laparoscopic settings. With further reference to FIG. 1A, the conduit 24 may be adapted for coupling the vacuum source 12 to an outlet port of the tower connector device 18 and may be sized and shaped for generating negative pressure and suction at levels required during open surgery. For instance, the conduit 24 may be tubing with a 1 inch diameter or another size commonly used for joining to a vacuum source adapted for use in open surgery. The conduits 22, 24 may be extruded from a single piece of material, e.g., a unitary piece of synthetic resin or similar extrudable material. The conduits may be advantageously and hygienically disposed of after a single use, without the necessity of handling contaminated material.

The flow regulator device 26 of the present disclosure, according to certain implementations, may be configured as a flow restrictor, valve or other suitable flow affecting arrangement, and may be associated with or integrally formed with the tower connector device 18. As described, the flow regulator device 26 may regulate negative pressure and suction generated by the vacuum source 12 so that the level of negative pressure/suction delivered to an end effector 16 is safe for laparoscopic settings. The device includes at least two ports: a vacuum port and an inlet port, as well as a flow control device. The vacuum port may be adapted to fluidly couple to the vacuum source 12, while the inlet port may be adapted to fluidly couple to an end effector 16. These ports may fluidly couple to one another, and the flow rate adjuster may operate to adjust a level of negative pressure, and therefore suction, delivered by the vacuum source to the inlet port to a reduced suction level. By use of the flow regulator device 26, the end effector 16 receives a level of active suction for removing smoke from a body cavity during laparoscopic surgery that otherwise would not be possible by the use of a vacuum source 12 adapted for open surgery (e.g., a vacuum source delivering at least 25 ft$^3$/min of suction). According to certain implementations, the flow rate adjuster is configured to reduce a diameter of a fluid pathway associated with an inlet port for the end effector 16. For instance, an initial diameter of an inlet for laparoscopic attachments (e.g., conduits or end effector tubing) may be about 5 mm, and the flow rate adjuster may be configured to reduce the diameter down to about 0.1 mm, thereby adjusting the rate of active suction available to the end effector 16. In addition or alternatively, the initial diameter of the inlet for laparoscopic attachments may allow for a maximum suction rate of about 0.35 ft$^3$/min (i.e., about 10 liters per minute) and may be reduced to a diameter of 0, i.e., to turn off the active suction.

Figure 2:
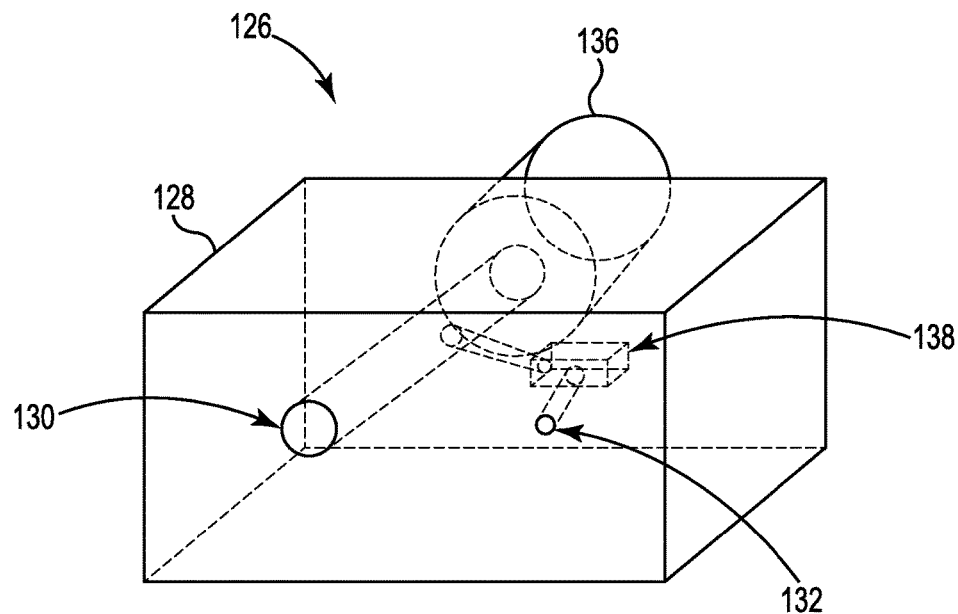
FIG. 2 illustrates a schematic of a flow regulator device according to other implementations of the present disclosure.

According to certain implementations, the flow regulator device 26, or a portion thereof, may be incorporated in a faceplate of the type that commonly forms a component of the tower connector device 18. FIG. 2 depicts a faceplate 28 according to the present disclosure, which may include the ports and/or the flow rate adjuster of the regulator device 26. In FIG. 2, the faceplate 28 includes end effector port 30, optionally ports 32, a vacuum port 36, an end effector port flow rate adjuster 38, optionally flow rate adjuster 40, a vacuum port flow rate adjuster 42, inputs 44 and a display 46. The end effector port 30 may be sized and shaped to receive the conduit 22 or another connection device joined to the end effector 16 configured for laparoscopic surgery, and the end effector port 30 may be fluidly coupled to the vacuum port 36 configured to joint to the vacuum source 12. The vacuum port 36 may have a diameter commonly associated with vacuum sources used in open surgery, and for example, may have a diameter of 1 inch or greater. Consequently, the diameter of the vacuum port 36 is relatively larger than a diameter of the end effector port 30. The end effector port flow rate adjuster 38 may be configured as a manually (e.g., via a control knob) or automatically operable adjustment device and may be used to adjust a diameter of the end effector port 30 to control a rate of suction delivered to the end effector 16. For instance, an initial diameter of the end effector port 30 may be about 5 mm, and the flow rate adjuster 38 may be configured to reduce the diameter down to about 0.1 mm, thereby adjusting the rate of active suction available to the end effector 16. While the faceplate 28 is depicted as including a vacuum port 36, in other instances, this port may be arranged on another portion of the tower connector device 18 while maintaining a fluid connection to the end effector port 30.

As described, the faceplate 28 may additionally include other ports and flow rate adjusters. For example, the flow regulator device 26 or the faceplate 28 may include a port 32 for open surgery configured to fluidly couple to end effectors used in open surgery. In this example, a diameter of the port 32 is configured to receive the negative pressure generated by the vacuum source at the level of suction for removing smoke during open surgery. In addition, the port 32 may be fluidly coupled to the vacuum port 36, and the flow rate adjuster 40 may be configured similarly to the flow rate adjuster 38 and may adjust the flow rate delivered to the open surgical end effector during open surgery by controlling a diameter of the port 32. The vacuum port flow rate adjuster 42 may be configured to control a diameter of the vacuum port 36, which may be provided as an additional measure for controlling the negative pressure and suction to the end effector 16. Inputs 44 may be communicatively coupled to electrical components such as sensors associated with the ports 30, 32, and 36 for sensing pressure/suctions rates at the ports: and to the display 46, which may be a digital or analog display device, or an LED display. Further, the components of the evacuation system 10 may be coupled to suitable microprocessor or integrated circuit components.

Turning to FIG. 2, another embodiment of a flow regulator device 126 is depicted, which may be a self-contained device adapted to be joined (e.g., plugged-in) to the tower connector device 18, e.g., via the vacuum port 36, or to another component of the evacuation system 10. Accordingly, the flow regulator device 126 may couple between an end effector 16 proximate a patient and the tower connector device 18 or the vacuum source 12, which may or may not be coupled to the tower connector device 18. The flow regulator device 126 may include a housing 128, an open surgical procedure port 130, a laparoscopic procedure port 132, a vacuum port 136, a laparoscopic flow regulator 138 as well as other flow regulators.

The housing 128 of the flow regulator device 126 may be configured with a size and shape allowing the device to be positioned adjacent to and optionally joined directly to a port defined in the tower connector device 18 or in a vacuum source 12 or a port defined in a device fluidly coupled to the vacuum source 12.

With respect to the open surgical port 130, this port may be adapted to join to tubing or another conduit that is fluidly coupled to a hand-held device used for open surgery. With respect to the laparoscopic surgical port 132, this port may be adapted to join to a laparoscopic device used to evacuate smoke or fluids from a closed surgical setting. The diameter of these surgical ports may differ from each other based on the level of negative pressure used during open procedures compared to laparoscopic procedures. For instance, the laparoscopic surgical port may have a relatively smaller diameter compared to the open surgical port due do the laparoscopic device receiving a lower level of negative pressure compared to the hand-held devices used in open surgeries. As described, a diameter of a laparoscopic port 132 may be about 5 mm, and the diameter of the open surgical port 130 may be relatively larger, e.g., at least 6 mm. The vacuum port 136 may be adapted to join to the vacuum source 12 or to a port defined by a device fluidly coupled to the vacuum source.

Port walls of the device may define openings of differing sizes that join to one another in order to regulate the negative pressure/suction transferred to the suction devices during operation. By varying the diameter of the openings within the device, the negative pressure/suction delivered to the end effector 16 or other evacuation devices may be defined and controlled. As described, the relative diameters of the ports 130, 132 may differ from one another based on the negative pressure requirements of the respective end effectors. In addition, the vacuum port 136 may be sized and shaped so that the vacuum port fluidly joins to the open and laparoscopic ports. With reference to FIG. 2, the diameter of the vacuum port 136 may be relatively larger than the diameters of both the open and laparoscopic surgical ports 130, 132. The open surgical port 130 may join directly to the vacuum port 136, and a wall may be arranged between a connection point where the vacuum port 136 joins to the open surgical port 130, thus accounting for the difference in diameter between these ports. The laparoscopic surgical port 132 may fluidly couple to the vacuum port 136 directly or via the open surgical port 130 as shown in FIG. 2. The laparoscopic flow regulator 136 may join to the laparoscopic surgical port 132 for use in controlling an internal diameter of the laparoscopic surgical port 132.

Figure 3A:
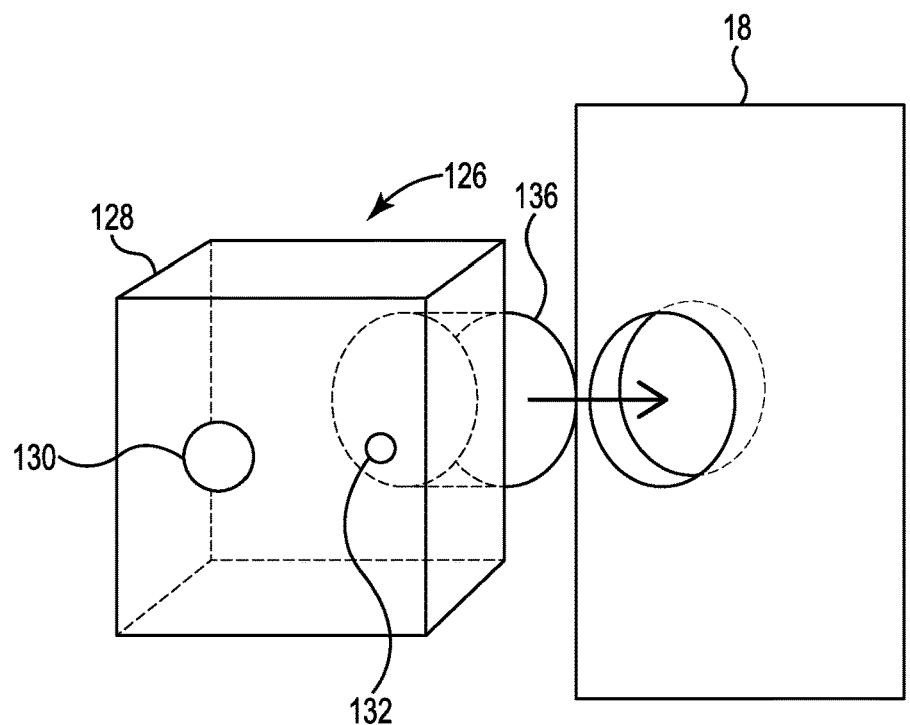
FIG. 3A illustrates an isometric view of a schematic of the flow regulator device of FIG. 2 and its arrangement relative to a vacuum source.
Figure 3B:
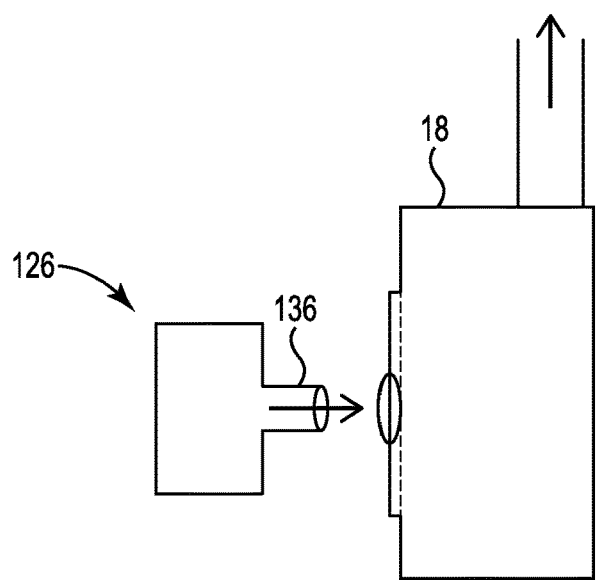
FIG. 3B illustrates a side view of the schematic of the flow regulator device and vacuum source of FIG. 3A.

Turning to FIG. 3A, the flow regulator device 126 and the tower connector device 18 are illustrated in an isometric view, and the vacuum port 136 of the flow regulator device 126 may be joined to or plugged-in to the vacuum port 36 (e.g., outlet) of the tower connector device. FIG. 3B illustrates a side view of the flow regulator device 126 proximate the tower connector device 18. Upon joining the flow regulator device 126 to the tower connector device, the tower connector device 18 may operate in substantially the same manner as the flow regulator device 26.

In use, the negative pressure generated by the vacuum source 12 is lower between the vacuum source 12 and the tower connector device 18 and/or the flow regulator device 26/126 than between the flow regulator device 26/126 and the end effector 16 and/or the abdominal cavity. In some embodiments, the evacuation system 10 may be thought of and/or referred to as a hybrid system comprising or utilizing typical evacuation or extraction vacuum pressures as well as reduced evacuation pressures (e.g., reduced suction). The portion of the system exhibiting the reduced negative pressure is useful, for example, in helping to reduce tissue dissection in the abdominal cavity, and the portion with the greater negative pressure (e.g., increased suction) helps provide for substantially complete evacuation and filtration of gaseous and fluid byproducts or noxious vapors flowing from the surgical site in the abdominal cavity through and/or into the tower connector device 18, disposal vessel 20 and filter 21. Further, the evacuation system 10 by use of collection and filtration devices may decontaminate fluids and gasses from surgery and enable the air and fluid end products to be released so that, for instance, the filtered and processed air from surgery may be released into the atmosphere (e.g., outside air) and the filtered and processed fluids from surgery may be released into sewer systems. For instance, as carbon dioxide gas exits the body cavity where the laparoscopic surgery takes place, the gas moves through the evacuation system 10 components where particulates are removed, e.g., through filtration (HEPA, ULPA and/or water filtration), and the gas may be further decontaminated using UV treatment. In some cases the decontamination process may occur before, during or after gases/fluids reach the vacuum source 12, or combinations thereof.

In some implementations, the evacuation system 10 may include an insufflator, or may be used in connection with such a device. In this case, a sensing and control system may be used to sense a level of pressure within a body cavity undergoing surgery and control a level of pressure therein by controlling the flow regulator device 26/126 and the insufflator. For instance, based on a selected pressure level to be maintained in the body cavity, the sensing and control system may use the flow regulator device 26/126 to regulate the negative pressure received by the end effector 16 from the vacuum source 12 (e.g., by controlling an internal diameter of the laparoscopic end effector inlet port) as well as the insufflator to regulate pressure delivered to the body cavity to achieve and maintain the selected pressure. In this implementation, the sensing and control system may allow for an active suction to be delivered to the body cavity at acceptable rates of active suction/negative pressure levels, such as suction rates of up to 10 liters per minute or at selected pressure differentials between the vacuum source and the body cavity, such as a pressure differential of 1 mmHg or more. For instance, consider 15 mmHg of pressure within the surgical site, pre-set in the insufflator and a 1 mmHg negative pressure (or slightly more negative pressure) provided by the vacuum source 12. This is in contrast to 15 mmHg within the abdomen based on the pre-set pressure regulator in the insufflator which continues to add CO2 to maintain the 15 mmHg pre-set pressure, and the outside air in the operating room which, by convention is considered as 0.0 mmHg. This first example is a pull (active suction) whereas the second example is a push (positive pressure gradient).

According to further implementations, the evacuation system 10 may be configured to control a level of negative pressure/active suction by controlling the operation of the vacuum source 12. For example, the evacuation system 10 may additionally or alternatively regulate the negative pressure generated by the vacuum source 12. In yet further implementations, the evacuation system 10, when used in combination with the tower connector device 18 may regulate the negative pressure at the vacuum port 32 such as by regulating the diameter of the port using the vacuum port flow rate adjuster 42.

Generally, in an operating room environment a noise level of 55 dB or less may be preferred, but this level may be varied. In some embodiments, the shape and/or size of the system components, e.g. tubing, openings, valves, etc., and/or flow rates and/or pressure gradients may be selected to sonically tune the evacuator and/or the evacuation system, i.e. balance optimal air flow and noise.

In another use of the system of the present invention, it may be used at a workstation or the like, or on or in a containment vessel or the like, to remove fumes or smoke. Such workstations and vessels may be used, for example, for cleaning components in the computer industry or for performing experiments or tasks in which noxious fumes are emitted.

The present invention may be embodied in other specific forms without departing from the essential spirit or attributes thereof. The described embodiments should be considered in all respects as illustrative, not restrictive.

What is claimed is:

1. An evacuation system for surgical settings comprising:
  a vacuum source configured to generate a negative pressure for delivering a level of suction for removing smoke during open surgery;
  a flow regulator device fluidly coupled to the vacuum source, the flow regulator device comprising a vacuum port, an inlet port, and a flow rate adjuster; and
  a sensing and control system operatively associated with the vacuum source and the flow regulator and programmed to:
    cause delivery of a first level of suction via the flow regulator device based on a target pressure level to be maintained in a body cavity during laparoscopic surgery;
    sense a level of pressure at one or more of the vacuum port and the inlet port indicative of a pressure of the body cavity during laparoscopic surgery; and
    cause delivery of a second level of suction via the flow regulator device in response to a sensed level of pressure deviating from the target pressure, the first and second levels of suction being non-zero suction levels,
  wherein the vacuum port is adapted to fluidly couple to the vacuum source, the inlet port is adapted to fluidly couple to an end effector, the vacuum port and the inlet port are fluidly coupled, and the flow rate adjuster is operable to adjust a level of negative pressure delivered by the vacuum source to the inlet port to a reduced suction level such that the end effector receives a level of active suction for removing smoke from the body cavity during laparoscopic surgery.

2. The evacuation system of claim 1, further comprising a tower connector device adapted for use in operating rooms, wherein the flow regulator device forms a portion of the tower connector device.

3. The evacuation system of claim 2, wherein the tower connector device further comprises a faceplate, and wherein at least the inlet port and the flow rate adjuster are arranged therein.

4. The evacuation system of claim 3, wherein the tower connector device further comprises the vacuum port.

5. The evacuation system of claim 3, wherein the tower connector device is communicatively coupled to a microprocessor or integrated circuit components adapted to measure the level of suction at the inlet port in response to operation of the flow rate adjuster.

6. The evacuation system of claim 1, wherein a diameter of the vacuum port is larger than a diameter of the fluidly coupled inlet port, and wherein the flow rate adjuster is configured to reduce the diameter of the inlet port.

7. The evacuation system of claim 6, wherein the flow rate adjuster of the flow regulator device is configured for manual operation by a user.

8. The evacuation system of claim 6, wherein the flow regulator device further comprises an open surgery port adapted to fluidly couple to an end effector configured for open surgery, wherein a diameter of the open surgery port is configured to receive the negative pressure generated by the vacuum source at the level of suction for removing smoke during open surgery.

9. The evacuation system of claim 6, wherein the flow regulator device is communicatively coupled to a microprocessor or integrated circuit components adapted to measure the level of suction at the inlet port.

10. The evacuation system of claim 1, wherein:
  the evacuation system defines a fluid pathway between the vacuum source and effector;
  the flow rate adjuster is arranged along the fluid pathway and configured to adjust a diameter of the fluid pathway;
  in a first configuration, the diameter of the fluid pathway is a first diameter, thereby causing the delivery of the first level of suction; and
  in a second configuration, the diameter of the fluid pathway is a second diameter, thereby causing the delivery of the second level of suction.

11. The evacuation system of claim 10, wherein:
  the fluid pathway comprises a first fluid pathway defined between the vacuum source and the vacuum port of the flow regulator device and a second fluid pathway defined between the inlet port of the flow regulator device and the end effector; and
  the first fluid pathway and the second fluid pathway have different diameters.

12. The evacuation system of claim 1, wherein:
  the target pressure level comprises a pressure gradient between the body cavity and the vacuum source; and
  the second level of suction caused by the sensing and control system is configured to maintain the pressure gradient.

13. An evacuation system for surgical settings comprising:
  a vacuum source configured to generate a negative pressure for delivering a level of suction of at least 25 cubic feet per minute;
  a flow regulator device fluidly coupled to the vacuum source, the flow regulator device comprising a vacuum port, an inlet port, and a flow rate adjuster; and
  a sensing and control system operatively associated with the vacuum source and the flow regulator and programmed to:
    cause delivery of a first level of suction via the flow regulator device based on a target pressure level to be maintained in a body cavity during laparoscopic surgery;

sense a level of pressure at one or more of the vacuum port and the inlet port indicative of a pressure of the body cavity during laparoscopic surgery; and cause delivery of a second level of suction via the flow regulator device in response to a sensed level of pressure deviating from the target pressure, the first and second levels of suction being non-zero suction levels, wherein the vacuum port is adapted to fluidly couple to the vacuum source, the inlet port is adapted to fluidly couple to an end effector, the vacuum port and the inlet port are fluidly coupled, and the flow rate adjuster is operable to adjust a level of negative pressure delivered by the vacuum source to the inlet port to a reduced suction level such that the end effector receives a level of suction for removing smoke from a body cavity of up to 0.35 cubic feet per minute.

14. An evacuation system for surgical settings comprising:
- a vacuum source configured to generate a negative pressure for delivering a level of suction for removing smoke during open surgery;
- a disposal vessel configured to hold fluid byproducts from surgery;
- a decontamination area configured to decontaminate gaseous byproducts from surgery;
- a flow regulator device, the flow regulator device comprising a vacuum port, an inlet port, and a flow rate adjuster;
- an end effector configured for insertion into a body and for removing smoke from a body cavity during laparoscopic surgery;
- a fluid pathway fluidly coupling the vacuum source, the disposal vessel, the decontamination area, the flow regulator device, and the end effector; and
- a sensing and control system operatively associated with the vacuum source and the flow regulator and programmed to:
  - cause delivery of a first level of suction via the flow regulator device based on a target pressure level to be maintained in a body cavity during laparoscopic surgery;
  - sense a level of pressure at one or more of the vacuum port and the inlet port indicative of a pressure of the body cavity during laparoscopic surgery; and
  - cause delivery of a second level of suction via the flow regulator device in response to a sensed level of pressure deviating from the target pressure, the first and second levels of suction being non-zero suction levels, wherein the vacuum port of the flow regulator couples to the vacuum source, the inlet port is adapted to fluidly couple to the end effector, the vacuum port and the inlet port are fluidly coupled, and the flow rate adjuster is operable to adjust a level of negative pressure delivered by the vacuum source to the inlet port to a reduced suction level such that the end effector receives a level of active suction for removing smoke from the body cavity during laparoscopic surgery.

15. The evacuation system of claim 14, wherein the decontamination area receives gaseous byproducts from the end effector and decontaminates the gaseous byproducts by ultraviolet treatment.

16. The evacuation system of claim 14, wherein the flow regulator device forms one of: a portion of a tower connector device adapted for use in operating rooms, a housing adapted to join directly to an outlet of the vacuum source, or a housing adapted to join directly to the tower connector device adapted for use in operating rooms.

17. The evacuation system of claim 16, wherein the flow regulator device is communicatively coupled to a microprocessor or integrated circuit components adapted to measure the level of suction at the inlet port.

18. The evacuation system of claim 17, wherein the flow rate adjuster of the flow regulator device is configured for manual operation by a user.

19. The evacuation system of claim 18, wherein a diameter of the vacuum port is larger than a diameter of the fluidly coupled inlet port, and wherein the flow rate adjuster is configured to reduce the diameter of the inlet port.

20. The evacuation system of claim 19, wherein the flow regulator forms a portion of the tower connector device, wherein the tower connector device further comprises a faceplate, and wherein at least the inlet port and the flow rate adjuster are arranged therein.

* * * * *